United States Patent [19]

Miller

[11] Patent Number: 4,834,095

[45] Date of Patent: May 30, 1989

[54] PROBE UNIT FOR ELECTRO-SURGICAL DEVICE

[75] Inventor: Alan N. Miller, New City, N.Y.

[73] Assignee: IPCO Corporation, White Plains, N.Y.

[21] Appl. No.: 156,479

[22] Filed: Feb. 16, 1988

[51] Int. Cl.$^4$ ............................................. A61B 17/36
[52] U.S. Cl. ............................ 128/303.14; 128/303.17
[58] Field of Search ............ 128/303.1, 303.14–303.17

[56] References Cited

U.S. PATENT DOCUMENTS

| | | | |
|---|---|---|---|
| 3,807,404 | 4/1974 | Weissman et al. | 128/303.14 |
| 4,174,714 | 11/1979 | Mehl | 128/303.17 |
| 4,301,801 | 11/1981 | Schneiderman | 128/303.14 |
| 4,427,006 | 1/1984 | Nottke | 128/303.17 |
| 4,655,215 | 4/1987 | Pike | 128/303.17 |
| 4,711,239 | 12/1987 | Serochenko et al. | 128/303.17 |
| 4,719,914 | 1/1988 | Johnson | 128/303.17 |

FOREIGN PATENT DOCUMENTS

| | | | |
|---|---|---|---|
| 2262209 | 7/1973 | Fed. Rep. of Germany | 128/303.17 |
| 2442605 | 3/1976 | Fed. Rep. of Germany | 128/303.17 |
| 8202488 | 8/1982 | World Int. Prop. O. | 128/303.17 |

*Primary Examiner*—Max Hindenburg
*Attorney, Agent, or Firm*—Goodman & Teitelbaum

[57] ABSTRACT

A probe unit for an electro-surgical device to apply high level frequency voltage to an operating area, the probe unit including an operative end portion provided with a forward cutting tip, and a rear housing connector portion provided with a ferrule rotatably connected to the remaining body portion thereof, a rear end of the operative end portion being threadingly engaged with the ferrule for rotation therewith and for easy removal thereof so that the operative end portion can be sterilized and then re-engaged onto the ferrule of the rear housing connector portion. The operative end portion has an elongated length considerably longer than the rear housing connector portion to prevent cross-contamination of a user and/or patient when the probe unit is being used. The body of the operative end portion is tapered with a rear enlarged portion thereof being provided with laterally extending fins thereabout to provide for uniform curing and a uniform cross-section thereof. The body portion of the rear housing connector portion is provided with lamps to indicate when the high level frequency voltage is being applied at the cutting tip. In one modified embodiment, the operative end portion includes an on/off switch, and in another modified embodiment, the operative end portion is provided with a releasable wedge connecting engagement to permit the replacement of the cutting tip.

14 Claims, 6 Drawing Sheets

PROBE UNIT FOR ELECTRO-SURGICAL DEVICE

BACKGROUND OF THE INVENTION

This invention relates a probe unit for electro-surgical devices and, more particularly, to a probe unit having an operative end portion which is removable so that the operative end portion can be sterilized and replaced thereon, the operative end portion being hand-held in use and being rotatable with respect to a rear housing connector portion of the probe unit.

Electro-surgical devices and instruments which are capable of being used for carrying out medical or dental operations are well known in the art, such a device being disclosed in U.S. Pat. No. 4,301,801. This patent shows a probe unit connected to an electrosurge generator so that a source of high level frequency voltage is applied to the cutting tip of the probe unit which can be manually controlled.

More specifically, U.S. Pat. No. 3,807,404 discloses a probe unit having a disposable probe tip which is rotatable relative to the hand-held portion. The probe tip includes a closed loop in the form of a cutting tip.

However, none of the prior art probe units are provided with an operative end portion which can be sterilized, where as mentioned above, the prior art probe tips are of the disposable type. Furthermore, it has been found that a more convenient probe unit construction is desired in order for the operative end portion to more easily rotate relative to the rear housing connector portion of the probe unit when in use, where the above-mentioned U.S. Pat. No. 3,807,404 provides for a frictional retention of the operative end portion of the probe unit which does not provide for an easy rotation thereof.

SUMMARY OF THE INVENTION

Accordingly, it is an object of the present invention to provide a probe unit for an electro-surgical device which avoids the problems of the prior art devices.

Another object of the present invention is to provide a probe unit which has a simple construction, and is economical to manufacture.

Still another object of the present invention is to provide a probe unit which includes an operative end portion which can be removed and sterilized, and then repositioned on the probe unit.

Still a further object of the present invention is to provide a probe unit which has an operative end portion capable of being easily rotated relative to a rear housing connector portion of the probe unit.

Still another object of the present invention is to provide a probe unit which has an operative end portion with an elongated length considerably longer than the rear housing connector portion to prevent cross-contamination of the user and/or patient during use thereof, and to aid in the sterilization of the probe unit.

Yet another object of the present invention is to provide a probe unit as described above, wherein a portion of the operative end portion is provided with laterally extending fins to avoid heat sinks during the forming thereof so that there is provided a uniform curing, thus providing a uniform cross-section in the finished operative end portion.

And yet still another project of the present invention is to provide a probe unit as described above, wherein the operative end portion is threadingly engaged to a ferrule of the rear housing connector portion to prevent the parts from being pulled apart.

Another object of the present invention is to provide a probe unit as described above wherein the ferrule is rotatably secured to the remaining body portion of the rear housing connector portion to provide a free swivel arrangement to permit rotatable movement of the operative end portion without causing an increasing torque with respect to the connecting power cord extending from the rear housing connector portion.

Still another object of the present invention is to provide a probe unit which includes an on/off switch on the operative end portion.

Still a further object of the present invention is to provide a probe unit which includes means on the operative end portion to permit replacement of the cutting tip.

Briefly, in accordance with the present invention, there is provided a probe unit for an electro-surgical device which includes an operative end portion provided with a cutting tip, and also includes a rear housing connector portion provided with a ferrule rotatably connected to the remaining body portion thereof. The operative end portion is threadingly engaged with the ferrule for easy removal thereof so that the operative end portion can be sterilized and then re-engaged to the rear housing connector portion. The operative end portion has an elongated length, considerably longer than the rear housing connector portion, with a portion of the operative end portion being provided with laterally extending fins to provide for uniform curing and a uniform cross-section thereof. The body portion of the rear housing connector portion is provided with lamp means to indicate when the high level frequency voltage is at a cutting tip.

In one embodiment of the present invention, the operative end portion is modified to include an on/off switch. In another embodiment of the present invention, the operative end portion is provided with means to permit the replacement of the cutting tip.

BRIEF DESCRIPTION OF THE DRAWINGS

With the above and additional objects and advantages in view, as will hereinafter appear, this invention comprises the devices, combinations and arrangements of parts hereinafter described by way of example and illustrated in the accompanying drawings of a preferred embodiment, in which.

In the various figures of the drawings, like reference characters designate like parts.

DETAILED DESCRIPTION OF THE PREFERRED EMBODIMENTS

Figure 1:
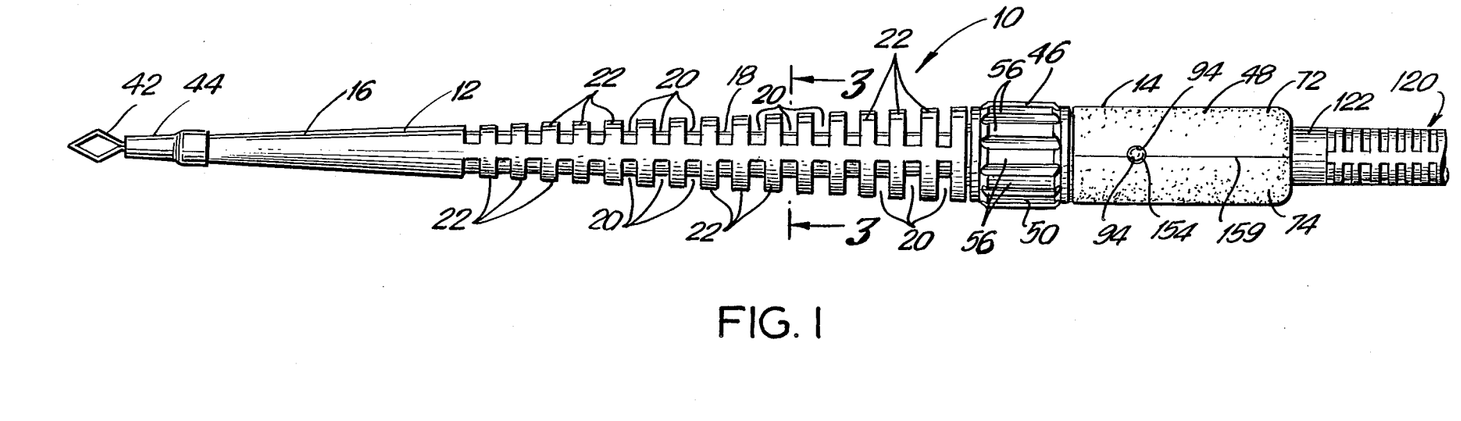
FIG. 1 is a perspective view showing a probe unit according to the present invention.
Figure 2:
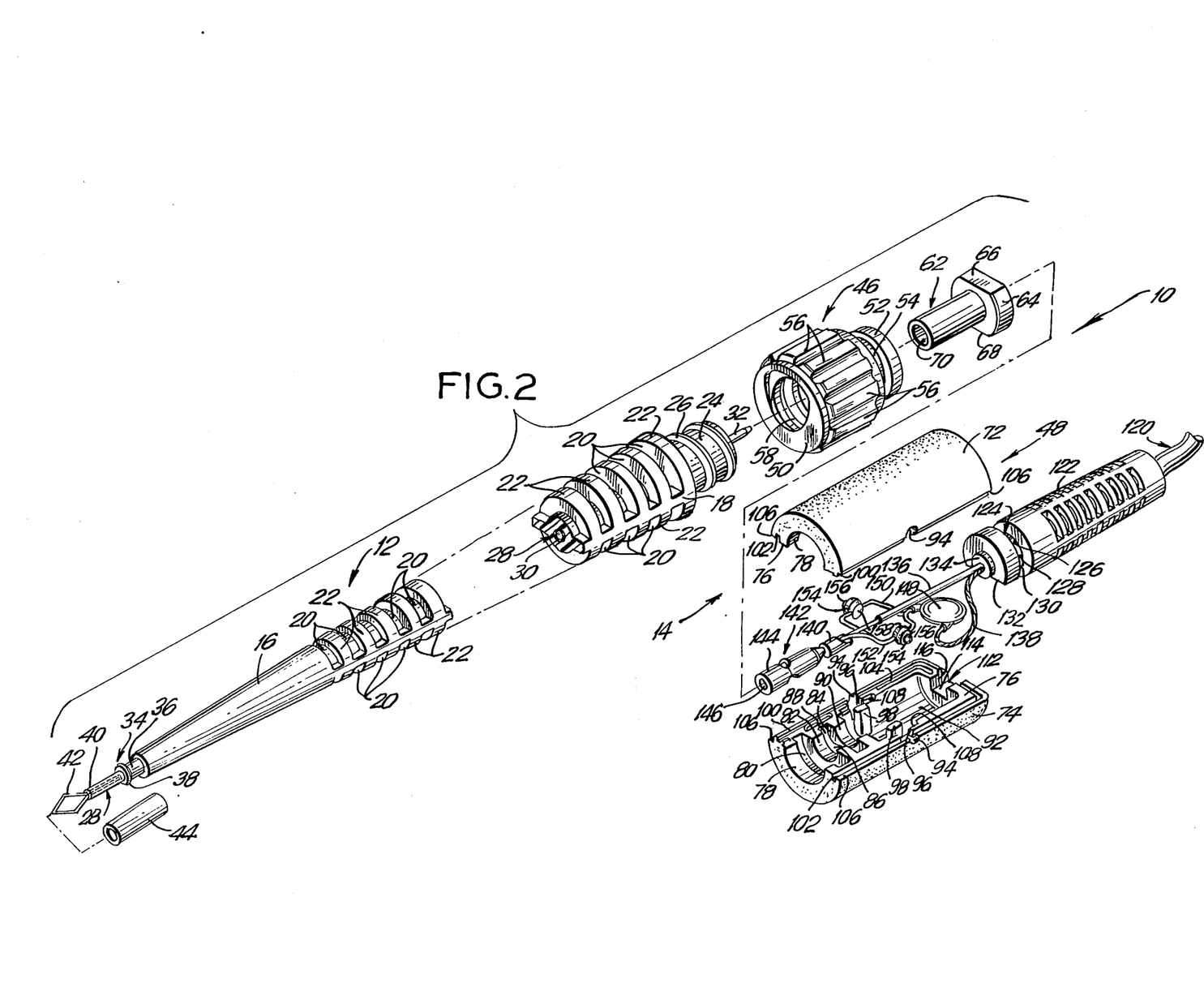
FIG. 2 is an exploded perspective view of the probe unit shown in FIG. 1.

Referring to the drawings, FIGS. 1 and 2 show a probe unit 10 in accordance with the present invention. The probe unit 10 includes an operative end portion 12 and a rear housing connector portion 14, which are removably secured together so that the operative end portion 12 can be removed and sterilized, and then repositioned thereon as set forth below.

The operative end portion 12 includes an elongated tapered cylindrical body 16 which is longer than the rear housing connector portion 14 to prevent cross-contamination of the use and/or patient when being used. The rear portion 18 of the body 16 is provided with a series of spaced apart grooves 20 on each side thereof to provide laterally extending fins 22 thereabout to avoid heat sinks during the formation thereof in the mold so that the curing process in the mold is uniform, thus providing a uniform cross-section in the finished body 16. It is noted, that the fins 22 are necessary to avoid the above-mentioned heat sinks because of the tapering construction of the body 16, where the fins 22 of the rear portion 18 have an increasingly larger diameter towards the rear thereof than the forward portion of the body 16.

The body 16 of the operative end portion 12 is fabricated from a non-conducting material, preferably a plastic such as polysulfone. The body 16 preferably has a textured surface.

A reduced end portion 24 extends longitudinally outwardly from the rear end of the rear portion 18 of the body 16, being formed integrally therewith. The end portion 24 is provided with an external thread 26, the funtion of which is set forth below.

Figure 3:
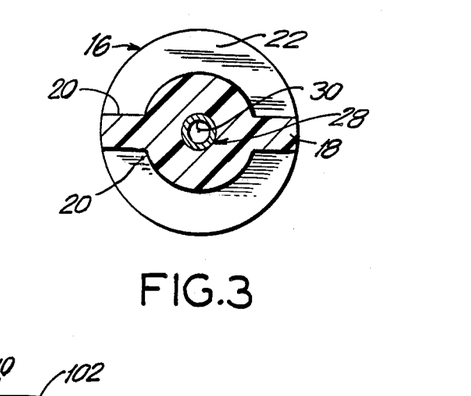
FIG. 3 is an enlarged cross-sectional view taken along line 3—3 of FIG. 1.

As best shown in FIG. 3, a tubular conductor 28 is enclosed within the body 16 in the center thereof and extends along the entire length of the body 16. The tubular conductor 28 is preferably fabricated from copper or like suitable conducting material. The tubular conductor 28 has a hole 30 therethrough, which also extends the entire length of the body 16 along the longitudinal axis thereof. The rear end of the conductor 28 is electrically connected in a suitable manner to a male connector pin 32 fabricated from a suitable metal. The forward end of the connector pin 32 is sealingly enclosed within the end portion 24, with the opposite free rear end of the connector pin 32 extending rearwardly outwardly from the end portion 24 along the longitudinal axis thereof, the function of which is described below.

The tip portion 34 at the forward end of the body 16 has a reduced portion 36 provided therein and a collar 38 at the front end thereof. The forward end 40 of the tubular conductor 28 extends outwardly from the collar 38 of the tip portion 34 of the body 16. A cutting tip 42 having a closed loop configuration at the front end thereof, has its legs secured in the hole 30 at the forward end 40 of the tubular conductor 28 by conventional means, such as by a crimp engagement, so that the cutting tip 42 makes electrical contact with the conductor 28, where it is noted that the cutting tip could be constructed in other shapes well-known in the art.

A sleeve 44, fabricated from a non-conducting material such as plastic, is heat-shrunk onto the forward end 40 of the conductor 28 and the tip portion 34, extending into the reduced portion 36 for securement thereof, to provide an insulation for the forward end of the operative end portion 12 as best shown in FIG. 1. The sleeve 44 also seals the forward end of the operative end portion 12. Thus, as indicated above, the operative end portion 12 is leakage-proof so that no fluid, such as blood, saliva, water and the like, can leak through the operative end portion 12 to the rear housing connector portion 14. Furthermore, the operative end portion 12, which is an integral unit, can be easily sterilized without causing any damage to the conductor 28 which is enclosed within the body 16 and the sleeve 44 in a waterproof arrangement.

The rear housing connector portion 14 includes a ferrule 46 at the forward end thereof, and a body portion 48 at the rear end thereof. The ferrule 46, preferably fabricated from a plastic material such as polysulfone, includes an enlarged forward cylindrical portion 50 and a cylindrical flange member 52 at the rear thereof connected together by a reduced cylindrical portion 54. The forward portion 50 is provided with rib members 56 around its periphery extending in the longitudinal direction of the probe unti 10 to facilitate an easy rotation of the ferrule 46 about its axis, as set forth below.

Figure 12:
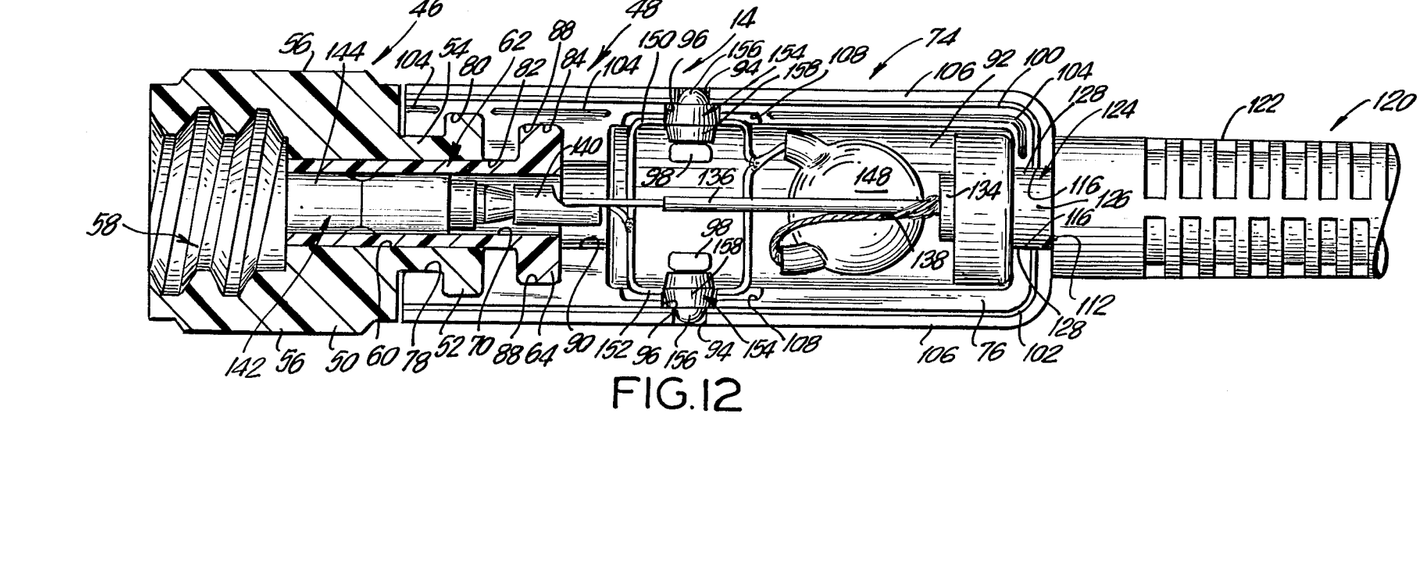
FIG. 12 is a cross-sectional view of the assmbled rear housing connector portion.

As best shown in FIG. 12, the forward portion 50 has an enlarged internally threaded hole 58 extending inwardly from the front end thereof, which is in communication with a smaller diameter hole 60 extending from the threaded hole 58 in the forward portion 50 through the reduced portion 54 and the flange member 52 to the rear end thereof. The rear hole 60 of the ferrule 46 rotatably receives the forward end of a tubular member 62 therein. The tubular member 62 is fabricated from a suitable material, either plastic or metal as required, and includes a flange 64 on the rear end thereof. The upper and lower sides of the flange 64 are provided with flat surface 66, 68, the function of which is described below. A hole 70 extends longitudinally through the tubular member 62 including the flange 64, the function of which will also be described hereinafter below.

The body portion 48 has a two-piece construction including an upper half 72 and a lower half 74. The upper and lower halves are substantially identical except for the openings in the rear ends thereof which will be explained below. Thus, it is thought necessary only to explain the features of one of the upper and lower halves 72, 74 for an understanding thereof. Each of the upper and lower halves 72, 74 is fabricated from a plastic material such as polysulfone, with each half having a textured outer surface. The halves 72, 74 are constructed to be matingly fitted together, and then to be ultrasonically welded, as explained below.

Figure 4:
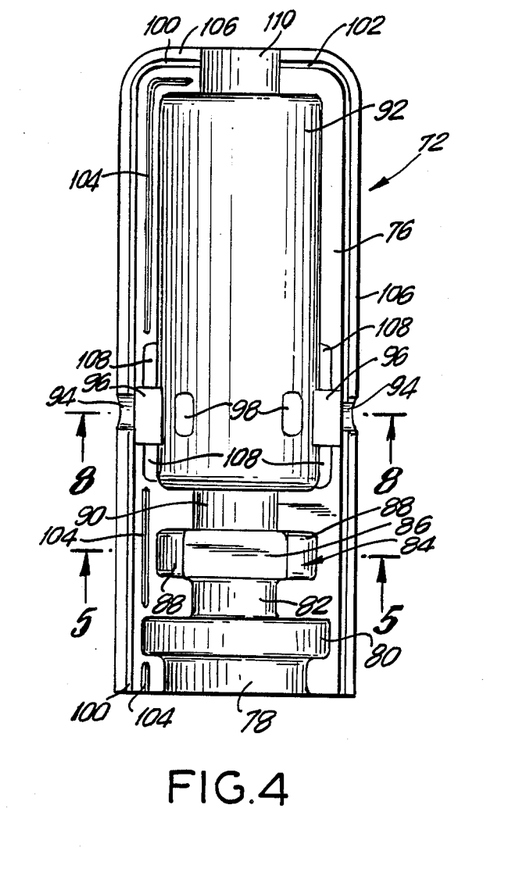
FIG. 4 is an inner plan view of the upper half of the body portion of the rear housing connector portion of the probe unit.
Figure 5:
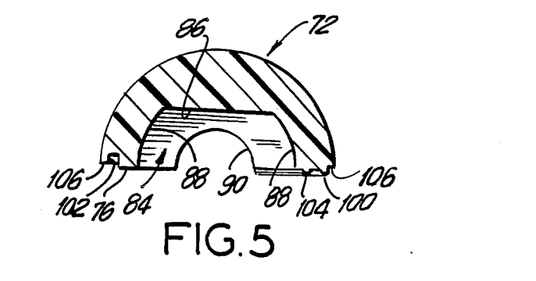
FIG. 5 is a cross-sectional view taken along line 5—5 of FIG. 4.
Figure 6:
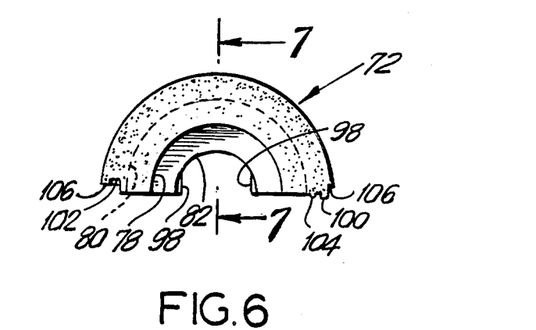
FIG. 6 is a forward end view of the upper half of the body portion shown in FIG. 4.
Figure 7:
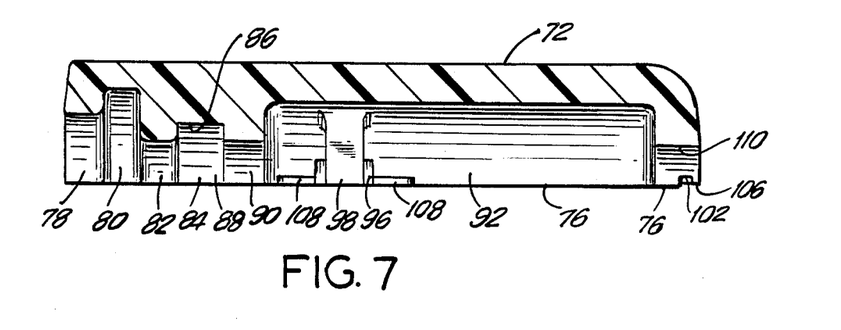
FIG. 7 is a cross-sectional view taken along line 7—7 of FIG. 6.

FIGS. 4–9 show the detailed construction of the upper half 72, which in most part will also apply to the lower half 74 as stated above. The upper half 72 is semi-circular and includes an upstanding wall 76 around the interior thereof which mates with a corresponding inner wall 72 of the lower half 74. As best shown in FIGS. 4, 6 and 7, a semi-circular opening 78 is provided in the front end of the upper half 76 which communicates with an enlarged semi-circular recess 80. The recess 80 communicates with a reduced semi-circular opening 82 which in turn communicates with an enlarged seat 84 having a flat top wall 86 connected to arcuate sidewalls 88, as best shown in FIG. 5. The seat 84 communicates with a reduced semi-circular opening 90 which in turn communicates with an enlarged semi-circular chamber 92.

Figure 8:
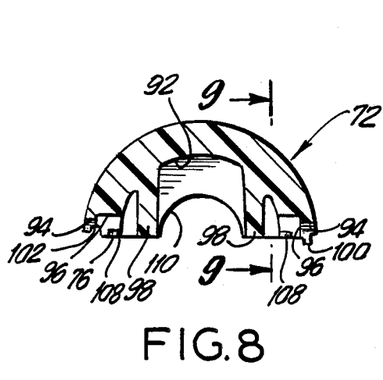
FIG. 8 is a cross-sectional view taken along line 8—8 of FIG. 4.
Figure 9:
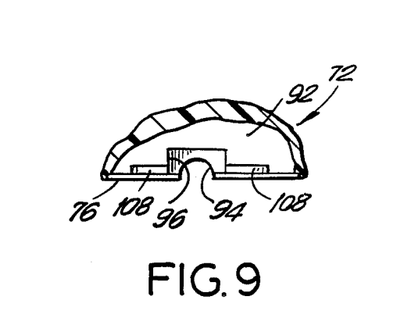
FIG. 9 is a cross-sectional view taken along line 9—9 of FIG. 8.

As best shown in FIGS. 4, 8 and 9, small semi-circular holes 94 are formed in opposite sides of the wall 76 extending from the outer surface of the upper half 72. The semi-circular holes 94 communicate with substantially rectangular shaped holes 96 also formed in the opposite sides of the wall 76 of the upper half 72 for communication with the chamber 92, the semi-circular holes 94 and the rectangular shaped holes 96 being in alignment with each other. A pair of spaced apart resilient tabs 98 extend from the top of the chamber 92 for alignment with the semi-circular holes 94 and rectangular shaped holes 96 so that one of the tabs 98 is associated with one semi-circular hole 94 and one rectangular shaped hole 96 on one side of the chamber 92, and the other tab 98 is associated with the other semi-circular hole 94 and other rectangular shaped hole 96 on the other side of the chamber 92, the function of which will be set forth below.

As best shown in FIGS. 4, 5, 6 and 9, a rib 100 is provided on one half of the inner surface of the wall 76, and a groove 102 is provided in the other half of the inner surface of the wall 76 so that the rib 100 and the groove 102 each have an L-shaped configuration extending from the forward end of the upper half 72 and along a portion of the rear end of the upper half 72. Additionally, energy directors 104 are provided between the rib 100 and the hollow interior of the upper half 72. It is further noted, that a recess 106 is formed around the periphery of the wall 76 extending from the rib 100 and groove 102 to the outer edge thereof. Furthermore, clearance spaces 108 are provided in the chamber 92 on opposite sides of the rectangular shaped holes 96.

Figure 10:
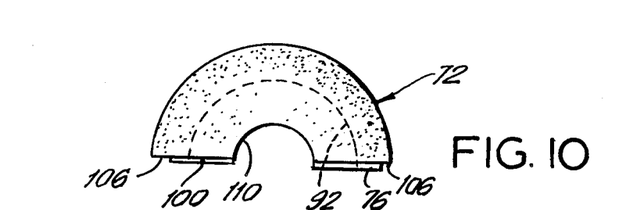
FIG. 10 is a rear end view of the upper half of the body portion.
Figure 11:
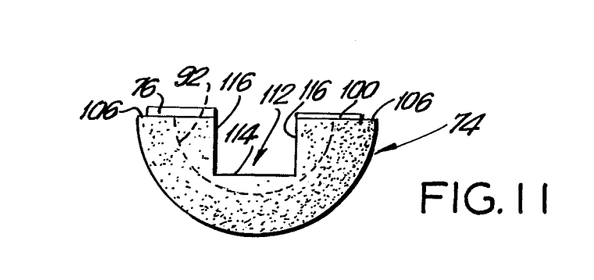
FIG. 11 is a rear end view of the lower half of the body portion.

The structure described above with respect to the upper half 72 is identical with the structure of the lower half 74. FIG. 10 shows the rear end of the upper half 72 having a semi-circular opening 110 therethrough in communication with the chamber 92, as indicated in FIGS. 4 and 7. However, FIGS. 2 and 11 show the rear end of the lower half 74 having a cornered opening 112 therethrough in communication with the chamber 92 so that the opening 112 has a flat bottom wall 114 and flat sidewalls 116, which are the only differences between the upper and lower halves 72, 74. The function of the cornered opening 112 will be set forth hereinafter below.

Referring to FIGS. 2 and 12, the electrical components of the probe unit 10 will now be discussed. The electrical power cord 120 has a flexible rubber-like tubular strain-relief sleeve 122 secured on the forward end thereof. It is noted, that the electrical power cord 120 is connected to the electro-surgical device, where the electrical energy can be supplied to the power cord 120 by means of a foot switch in the same manner as set forth in the above mentioned U.S. Pat. No. 4,301,801, to which reference may be made. The sleeve 122 includes a series of alterally running grooves provided in the periphery thereof to limit the flexibility of the sleeve 122 so that the electrical wires therein will not break. Additionally, a recessed seat 124 is provided near the forward end of the sleeve 122. The seat 124 has an arcuate upper surface 126, flat side surfaces 128 and a flat bottom surface 130. The forward end of the sleeve 122 also has a flat bottom surface 132, the function of these flat surfaces 128, 130 and 132 will be set forth below.

The front end of the sleeve 122 is provided with a reduced circular forwardly extending tip portion 134 from which extends a "hot" electrical wire lead 136 and a braided "ground" electrical wire lead 138, the leads 136, 138 being enclosed within the electrical power cord 120 in a conventional manner for connection to the electro-surgical device as set forth above. The forward end of the "hot" lead 136 is connected in a conventional manner directly to the rear end 140 of an electrical metal socket 142. The forward end of the socket 142 includes a female tubular member 144 provided with an opening 146 extending longitudinally therethrough to receive the above-mentioned male connector pin 32, as set forth below.

The forward end of the "ground" lead 138 is connected to the input terminal of a suitable capacitor 148. A pair of electrical wires 150, 152 are connected to the output terminal of the capacitor 148. The wires 150, 152 connect a pair of lamp means 154, such as conventional LED, in a parallel circuit arrangement to the rear end 140 of the socket 142 for engagement with the "hot" wire 136.

Referring to FIG. 12, the assembling of the rear housing connector portion 14 will now be discussed. The female tubular member 144 of the socket 142 is inserted into the hole 70 of the tubular member 62 from the rear end thereof in a suitable non-rotatable engagement therebetween so that the forward ends of the socket 142 and the tubular member 62 are in alignment with each other. The tubular member 62 is then inserted into the hole 60 in the ferrule 46, where it is noted that there is a rotational relationship between the tubular member 62 and the ferrule 46. The ferrule 46 and the tubular member 62 are then inserted into the lower half 74 of the body portion 48 so that the cylindrical portion 54 is received in the semi-circular opening 78, and the flange member 52 is received in the enlarged semi-circular recess 80 which permits rotation of the ferrule 46 relative to the lower half 74.

At the same time, the rear portion of the tubular member 62 is received in the reduced semi-circular opening 82 of the lower half 74, and the flange 64 of the tubular member 62 is received in the enlarged seat 84 of the lower half 74 so that the flat surface 68 of the flange 64 is disposed against the flat wall 86 of the sea 84 of the lower half 74 in order to prevent the rotation of the tubular member 62 relative to the lower half 74. In this placement, the rear end 140 of the socket 142 extends into the reduced semi-circular opening 90 of the lower half 74, and the "hot" lead 136 and the wires 150, 152 extend into the chamber 92.

The lamp means 154 are now positioned in the lower half 74 so that each lamp 156 of the lamp means 154 is in its associated semi-circular hole 94 of the lower half 74, and each lower housing 158 of the lamp means 154 is in its associated rectangular hole 96 of the lower half 74. Each housing 158 abuts against the outer walls of its associated rectangular hole 96 with the opposite end of each housing 158 being disposed against its associated resilient tab 98 in a force-fit therewith to hold the lamp means 154 within the lower half 74. The capacitor 148 is placed in the chamber 92 so that the lamp connecting portions of the wires 150, 152 are disposed in their associated clearance spaces 108 provided therefor.

The recessed seat 124 of the sleeve 122 is now placed in the cornered opening 112 in the rear end of the lower half 74 with the flat bottom surface 130 of the seat 124 being placed faced down against the flat bottom wall 114 of the opening 112, and the flat side surfaces 128 of the seat 124 being disposed against the flat sidewalls 116 of the opening 112, so that the sleeve 122 cannot rotate relative to the bottom half 74. The forward end of the sleeve 122 having the tip portion 134 thereon, is disposed within the chamber 92. The remaining rear portion of the sleeve 122 extends outwardly from the rear end of the lower half 74 so that the sleeve 122 is in a captured engagement with the lower half 74 and cannot be pulled longitudinally out from the lower half 74.

The upper half 72 is now placed on the lower half 74 in a mating engagement therewith so that the rib 100 of the upper half 72 is in alignment with the groove 102 of the lower half 74, and the rib 100 of the lower half 74 is in alignment with the groove 102 of the upper half 72. Additionally, the cylindrical portion 54 of the ferrule 46 is received in the semi-circular opening 78 of the upper half 72, and the flange member 52 is received in the enlarged semi-circular recess 80 of the upper half 72 in a manner which permits rotation of the ferrule 46 relative to the upper half 72, as well as the lower half 74. Furthermore, the rear portion of the tubular member 62 is received in the reduced semi-circular opening 82 of the upper half 72, and the flange 64 of the tubular member 62 is received in the enlarged seat 84 of the upper half 72 so that the flat surface 66 of the flange 64 is disposed against the flat wall 86 of the upper half 72 in order to further prevent the rotation of the tubular member 62 relative to the upper half 72, as well as the lower half 74. The rear end 140 of the socket 142 extends into the reduced semi-circular opening 90 of the upper half 72, and the "hot" lead 136 and the wires 150, 152 extend into the chamber 92.

Additionally, each lamp 156 of the lamp means 154 is positioned in its associated semi-circular hole 94 of the upper half 72, and each housing 158 of the lamp means 154 is positioned in its associated rectangular hole 96 of the upper half 72. Again, each housing 154 abuts against the outer walls of its associated rectangular wall 96 of the upper half with the opposite end of each housing 158 being dispose against its associated resilient tab 98 of the upper half 72 in a force-fit therewith to further hold the lamp means 154 in the upper half 72, as well as the lower half 74. The lamp connecting portions of the wires 150, 152 are also disposed in their associated clearance spaces 108 in the upper ahlf 72 which are provided therefor.

The arcuate upper surface 126 of the recessed seat 124 is received in the semi-circular opening 110 in the rear of the upper half 72, with the forward end of the sleeve 122 being disposed within the chamber 92 of the upper half 72, and the remaining rear portion of the sleeve 122 extending outwardly from the rear end of the upper half 72 so that the sleeve 122 is in a further captured engagement with the upper half 72, as well as the lower half 74. It is noted, that the recess 106 around the periphery of the upper half 72 mates with the recess 106 around the periphery of the lower half 74 to form a slot around the sidewalls and end portion of the body portion 48, as discussed below.

The assembled rear housing connector portion 14 is now placed in a conventional ultrasonic device to ultrasonically weld the upper half 72 to the lower half 74. During this welding operation the energy directors 104 on the upper and lower halves 72, 74 melt to bond the upper and lower halves 72, 74 together. It is noted, that during the melting of the energy directors 104, the upper and lower halves 72, 74 move closer together so that the ribs 100 on the upper and lower halves 72, 74 are moved into their respective grooves 102 in the upper and lower halves 72 and 74 for a mating engagement therebetween. Furthermore, the ribs 100 on the upper and lower halves 72, 74 prevent the melting plastic from flashing to the outside surfaces of the upper and lower halves 72, 74. It is additionally noted, that the above-mentioned slot formed by the recesses 106 is narrowed during the ultrasonic welding when the upper and lower halves 72, 74 move closer together to provide a reveal or recess 159 around the body portion 48, as shown in FIG. 1.

The ferrule 46 and the body portion 48 are now connected together as a unit, where the ferrule 46 is free to easily rotate relative to the body portion 48. Furthermore, the sleeve 122 is connected to the body portion 48 and is prevented from being rotated relative to the body portion 48, and is also prevented from being pulled longitudinally out from the body portion 48.

In the assembling of the probe unit 10, the male connector pin 32 is placed into the mouth of the operning 146 at the forward end of the female tubular member 144 of the socket 142. At the same time, the reduced end portion 24 at the rear of the rear portion 18 of the body 16 of the operative end portion 12 is placed into the mouth of the internally threaded hole 58 of the ferrule 46. The operative end portion 12 is now rotated so that the external thread 26 on the end portion 24 is threadingly engaged in the internally threaded hole 58. During this threading operation, the male conductor pin 32 is driven into the opening 146 of the female tubular member 144 to provide electrical contact therewith so that the power cord 120 is electrically connected to the cutting tip 42. Accordingly, after the above threading operation, the operative end portion 12 is connected to the ferrule 46, and rotates together with the ferrule 46 relative to the body portion 48.

In use, the user holds the operative end portion 12 with his fingers so that by turning the operative end portion 12 relative to the body portion 48, the user can position the cutting tip 42 at the forward end of the operative end portion 12 as desired during the cutting operation. The free swivel arrangement between the ferrule 46 and the body portion 48 permits the above rotation or tuning of the operative end portion 12 to be performed without causing an increasing torque with respect to the connecting power cord 120 extending from the rear of the body portion 48 of the rear housing connector portion 14. Obviously, the operative end portion 12 can easily be removed for sterilization thereof by merely unthreading the reduced end portion 24 thereof from the ferrule 46, and then can easily be replaced thereon in the manner set forth above.

Figure 13:
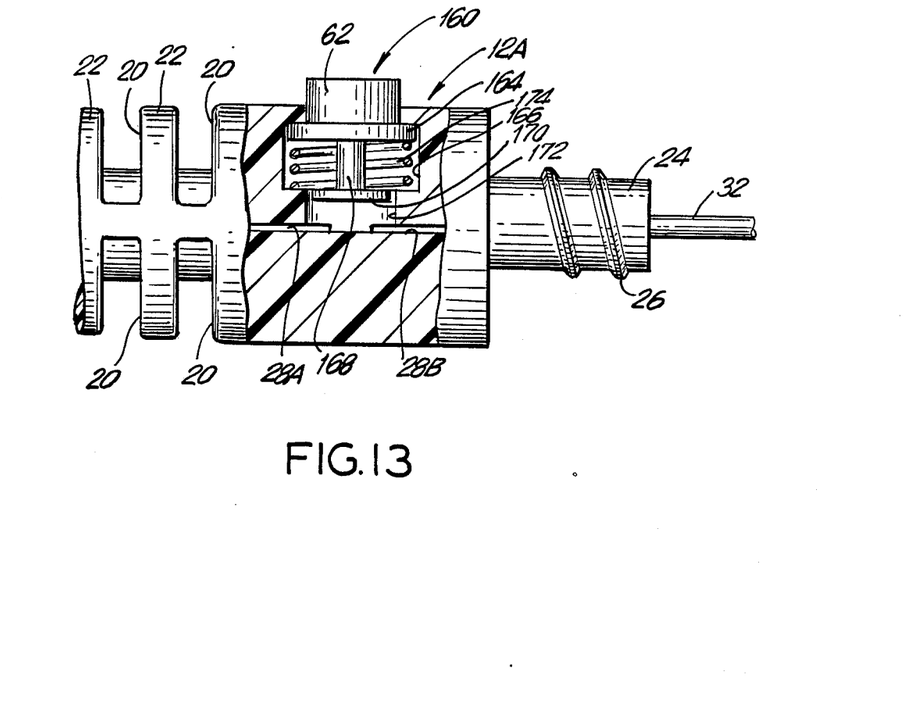
FIG. 13 is a fragmented, partially sectional view of a modified embodiment of the rear end of the operative end portion showing an on/off switch.

FIG. 13 shows an embodiment of a modified operative end portion 12A, where a rear portion of the operative end portion 12A is provided with an on/off switch 160. The on/off switch 160 includes a push button 162 fabricated from a nonconductive, preferably plastic, material. The push button 162 extends outwardly from the operative end portion 12A, being held therein by an enlarged collar 164 held captures within a seat 166 formed in the operative end portion 12A. Extending downwardly from the collar 164 of the push button 162 is a pin 168 having an enlarged flat metal contact 170 at the inner free end thereof The contact 170 is disposed in a smaller recess 172 formed in the operative end portion 12A in communication with the seat 166, the recess 172 being inwardly of the seat 166 and extending to the longitudinal axis of the operative end portion 12A.

The conductor which extends longitudinally along the longitudinal axis of the operative end portion 12A, is formed in two sections, a forward section 28A and a rear section 28B. The conductor sections 28A, 28B are separated from each other by a space less than the length of the contact 170 of the on/off switch 160. Thus, when the push button 162 is pushed downwardly into the operative end portion 12A, the metal contact 170 engages each of the end portions of the conductor sections 28A, 28B to make an electrical contact therebetween to supply the required high level frequency voltage to the cutting tip of the probe unit. Additionally, a coil spring 174 is disposed around the pin 168 within the seat 166. The spring 174 is positioned between the push button collar 164 and the bottom wall of the seat 166 so that the push button 162 and the contact 170 connected thereto are raised when the pursh button 162 is released by the user, thus breaking the electrical connection between the conductor sections 28A, 28B to cut off the high level frequency voltage to the cutting tip.

It is noted, that the on/off switch 160 can obviously be placed in any desired location along the length of the operative end portion 12A, when FIG. 13 is only for the purpose of illustration thereof.

Figure 14:
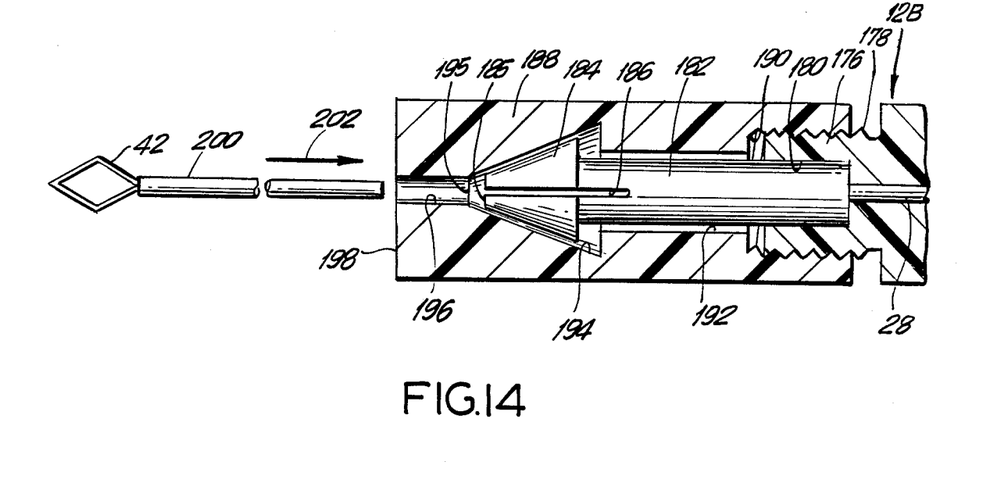
FIG. 14 is a fragmented, sectional view of a modified embodiment of the forward end of the operative end portion showing means for replacing the cutting tip.

FIG. 14 shows another embodiment of a further modified operative end portion 12B, where the forward end portion of the operative end portion 12B is provided with a reduced portion 176 having an external thread 178 thereon. The reduced portion 176 has a forward recess 180 therein to receive a real portion of a tubular metal member 182 therein. The tubular metal portion 182 is provided with a frustum-conical tip 184 which tapers to an increasingly larger diameter towards the rear thereof. A slit 186 extends longitudinally through the tip 184 and partly into the tubular member 182 so that the bifurcated sections of the tip 184 can be squeezed together. The rear end of the tubular member 182 is secured to the conductor 28 to provide an electrical connection therebetween.

A forward end member 188, fabricated from a nonconductive material such as plastic, encloses the tubular member 182 and tip 184 therein. The end member 188 includes an internally threaded recess 190 to threadingly receive the thread 178 of the reduced portion 176 therein. A longitudinally extending opening 192 extends from the recess 190 to receive the tubular member 182 therein. A forward conically shaped opening 194 communicates with the forward end of the opening 192 to receive the tip 184 therein, where the sidewalls of the opening 194 are tapered in a similar manner as the tip 184. However, the forward end 195 of the opening 194 has a smaller diameter than the forward end 185 of the tip 184 to provide a wedging engagement therebetween. A further opening 196 extends from the opening 194 to the front 198 of the end member 188.

The cutting tip 42 is electrically secured in a metal sleeve 200, so that the cutting tip 42 and the sleeve 200 are replaceable when desired.

In the assembling thereof, the rear end of the sleeve 200 is inserted from the front 198, in the direction of the arrow 202, into the opening 196 of the end member 188, and then through the tip 184 into the tubular member 182 as far as it will go therein. The forward end member 188 is then threaded back onto the thread 178 of the reduced portion 176 of the operative end portion 12B so that the conically shaped walls of the opening 194 engaged against the outer surface of the frustum-conical tip 184. The further threading of the forward end member 188 on the reduced portion 176, squeezes the bifurcated sections of the tip 184 together to clamp the sleeve 200 therebetween in a releasable wedging engagement to provide an electrical contact between the tip 184 and the sleeve 200. Thus, an electrical contact is made between the conductor 28 and the cutting tip 42. By releasing or loosening the engagement of the forward end member 188 on the reduced portion 176, the cutting tip 142 and the sleeve 200 can be removed therefrom and a new cutting tip and sleeve can be installed in the above manner.

Numerous alterations of the structures and the electrical components herein described will suggest themselves to those skilled in the art. However, it is to be understood that the present disclosure relates to preferred embodiments of the present invention, which are for the purpose of illustration only, and are not to be construed as a limitation of the present invention.

What is claimed is:

1. A probe unit for an electro-surgical device to apply high level frequency voltage to an operating area, said probe unit comprising:

an operative end portion having a front end provided with a cutting tip to apply the high level frequency voltage to the operating area, an electrical conductor connected to said cutting tip and extending longitudinally through said operative end portion;

said cutting tip and said electrical conductor being secured to said operative end portion for rotation therewith;

first means for sealing said conductor within said operative end portion in a waterproof arrangement to permit sterilization of said operative end portion without causing damage to said conductor;

said first means also providing a leakage-proof construction of said operative end portion to prevent fluid from leaking from said cutting tip, through said operative end portion, and then to a rear end of said operative end portion;

a rear housing connector portion provided with electrical means to supply the high level frequency voltage;

second means for removably securing said rear housing connector portion to said rear end of said operative end portion with said conductor being in electrical contact with said electrical means so that said operative end portion can be removed for said sterilization;

said second means preventing said rear housing connector portion from being pulled apart from said operative end portion;

said rear housing connector portion including a body portion;

rotatable means for rotating said operative end portion and said cutting tip relative to said body portion, said rotatable means including a ferrule rotatably secured to a front end of said body portion, said ferrule including a cylindrical flange member on a rear portion of said ferrule, said flange member being received within a cylindrical opening provided within said front end of said body portion for captured rotation therein to prevent said ferrule and said body portion from being pulled apart;

said second means including an external thread provided on said rear end of said operative end portion, and an internally threaded hole in a front end of said ferrule to threadingly receive said rear end of said operative end portion therein to provide a removable securement therebetween so that said ferrule, said operative end portion and said cutting tip rotate together relative to said body portion, and so that said conductor secured to said cutting tip rotates relative to said electrical means provided in said rear housing connector portion.

2. A probe unit according to claim 1, wherein said operative end portion includes an elongated cylindrical body longer than said rear housing connector portion to prevent cross-contamination between a user and a patient which said probe unit is being used.

3. A probe unit according to claim 2, wherein a rear end portion of said body of said operative end portion is provided with laterally extending fins thereabout to avoid heat sinks during formation thereof to provide a uniform curing thereof and a uniform cross-section.

4. A probe unit according to claim 2, wherein said body of said operative end portion is fabricated from a plastic-like material, and said rear housing connector portion includes a cylindrical body fabricated from a similar plastic-like material.

5. A probe unit according to claim 1, wherein said ferrule is provided with a rib means around its periphery extending in a longitudinal direction of said probe unit.

6. A probe unit according to claim 1, wherein said operative end portion includes an elongated cylindrical body longer than said rear housing connector portion to prevent cross-contamination between a user and a patient when said probe unit is being used, said body of said operative end portion being tapered so that said front end thereof has a smaller diameter than said rear end thereof.

7. A probe unit according to claim 6, wherein a rear end portion of said body of said operative end portion is provided with laterally extending fins thereabout to avoid heat sinks during formation thereof to provide a uniform curing thereof and a uniform cross-section.

8. A probe unit according to claim 1, wherein said rear end of said operative end portion has a male connector pin extending rearwardly therefrom, said male connector pin being electrically connected to said conductor, and said ferrule having a female tubular member therein, said female tubular member being electrically connected to said electrical means, said female tubular member receiving said male connector pin for rotation therein to provide an electrical contact therebetween when said rear end of said operative end portion is threaded into said internally threaded hole in said front end of said ferrule.

9. A probe unit according to claim 8, wherein said rear housing connector portion includes means to prevent rotation of said female tubular member relative to said body portion when said ferrule is rotated.

10. A probe unit according to claim 1, wherein said rear housing connector portion includes lamp means to indicate when the high level frequency voltage is being applied at said cutting tip.

11. A probe unit according to claim 10, wherein said body portion has a two half construction secured together by an ultrasonic weld, said lamp means being disposed in said body portion.

12. A probe unit according to claim 1, wherein said electrical means includes an electrical power cord provided with a strain-relief sleeve secured on a forward end of said power cord, means securing said sleeve to a rear portion of said rear housing connector portion to prevent said sleeve from being pulled apart from said rear housing connector portion, and means to prevent rotation of said sleeve relative to said rear housing connector portion.

13. A probe unit according to claim 1, wherein said operative end portion is provided with on/off switch means to control the supply of the high level frequency voltage to said cutting tip.

14. A probe unit according to claim 1, wherein said front end of said operative end portion is provided with releasable securement means to permit replacement of said cutting tip.

* * * * *